United States Patent
Minagawa

(10) Patent No.: US 10,058,635 B2
(45) Date of Patent: Aug. 28, 2018

(54) SURFACE TREATMENT AGENT AND MEDICAL DEVICE

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 144 days.

(21) Appl. No.: 14/857,171

(22) Filed: Sep. 17, 2015

(65) Prior Publication Data
US 2016/0096911 A1    Apr. 7, 2016

(30) Foreign Application Priority Data
Oct. 2, 2014   (JP) ................. 2014-204048

(51) Int. Cl.
| | |
|---|---|
| *A61L 29/06* | (2006.01) |
| *A61L 29/14* | (2006.01) |
| *A61M 25/00* | (2006.01) |
| *A61M 25/10* | (2013.01) |
| *C08L 63/00* | (2006.01) |
| *C08L 23/08* | (2006.01) |
| *C08L 63/08* | (2006.01) |
| *C08L 63/10* | (2006.01) |

(Continued)

(52) U.S. Cl.
CPC ............ *A61L 29/14* (2013.01); *A61L 29/06* (2013.01); *A61L 29/085* (2013.01); *A61L 29/145* (2013.01); *A61M 25/00* (2013.01); *A61M 25/10* (2013.01); *C08F 220/34* (2013.01); *C08L 23/0884* (2013.01); *C08L 63/00* (2013.01); *C08L 63/08* (2013.01); *C08L 63/10* (2013.01); *Y10T 428/1393* (2015.01)

(58) Field of Classification Search
CPC ... A61M 25/00; A61M 25/10; C08L 23/0884; C08L 63/00; C08L 63/08; C08L 63/10; Y10T 428/1352; Y10T 428/139; Y10T 428/1393; A61L 29/06; A61L 29/085; A61L 29/14; A61L 29/145
See application file for complete search history.

(56) References Cited

U.S. PATENT DOCUMENTS

2011/0106061 A1* 5/2011 Nielsen ................ A61L 29/085
                                                                    604/544

FOREIGN PATENT DOCUMENTS

| EP | 1206946 A1 | 5/2002 |
|---|---|---|
| JP | 7-100744 B2 | 11/1995 |
| JP | 9-66098 A | 3/1997 |

(Continued)

*Primary Examiner* — Walter Aughenbaugh
(74) *Attorney, Agent, or Firm* — Birch, Stewart, Kolasch & Birch, LLP

(57) ABSTRACT

Provided are surface treatment agents that enable surfaces with a chemically fixed lubricant to be produced instead of a resin coating which has drawbacks, such as that lubricity is reduced due to separation, peeling or the like of the coating during the movement within a vessel or tube; and medical devices, such as catheters, having a surface at least partially treated with such a surface treatment agent. The present invention relates to a surface treatment agent for medical devices which contains a copolymer of a hydrophilic functional group-containing monomer and an epoxy group-containing monomer.

11 Claims, 1 Drawing Sheet

(51) Int. Cl.
    *A61L 29/08*    (2006.01)
    *C08F 220/34*   (2006.01)

(56)            References Cited

FOREIGN PATENT DOCUMENTS

| JP | 10-110134 A    | 4/1998  |
| JP | 2007-289299 A  | 11/2007 |
| JP | 2009-518479 A  | 5/2009  |
| JP | 2011-188908 A  | 9/2011  |
| JP | 2015-57081 A   | 3/2015  |
| WO | WO 01/07097 A1 | 2/2001  |

* cited by examiner

SURFACE TREATMENT AGENT AND MEDICAL DEVICE

TECHNICAL FIELD

The present invention relates to surface treatment agents and medical devices such as catheters.

BACKGROUND ART

Catheters used in the medical field and the like, such as vascular catheters and urethral catheters for urethral catheterization, and the like are inserted into blood vessels, digestive tracts, tracheae, bile ducts, or ureters and used in aqueous solutions such as blood or body fluids. They are thus required to be able to be smoothly inserted without damaging tissues.

In this context, a low friction lubricant is applied to the surface of a catheter, or the surface is coated with a lubricant layer, before use (see Patent Literatures 1 to 3). However, these methods have drawbacks in that the surfaces thus formed have insufficient lubricity, and that since the lubricants are not chemically fixed on the surfaces of catheters, they are, for example, separated or peeled during the movement within a vessel or tube, so that the lubricity is reduced.

CITATION LIST

Patent Literature

Patent Literature 1: JP 2011-188908 A
Patent Literature 2: JP 2009-518479 T
Patent Literature 3: JP H07-100744 B

SUMMARY OF INVENTION

Technical Problem

The present invention aims to solve the aforementioned problems and provide surface treatment agents that enable surfaces with a chemically fixed lubricant to be produced instead of a resin coating which has drawbacks, such as that lubricity is reduced due to separation, peeling or the like of the coating during the movement within a vessel or tube, and to provide medical devices, such as catheters, having a surface at least partially treated with such a surface treatment agent.

Solution to Problem

The present invention relates to a surface treatment agent for medical devices, containing a copolymer of a hydrophilic functional group-containing monomer and an epoxy group-containing monomer.

The hydrophilic functional group is preferably at least one selected from the group consisting of a polyoxyalkylene group, a metal salt-containing hydrophilic group, a halogen salt-containing hydrophilic group, and a zwitterionic group. The metal salt-containing hydrophilic group is preferably at least one selected from the group consisting of an alkali metal salt-containing hydrophilic group and an alkaline earth metal salt-containing hydrophilic group. The halogen salt-containing hydrophilic group is preferably a chlorine salt-containing hydrophilic group.

The copolymer is preferably produced by photo- or thermally-induced radical polymerization.

The surface treatment agent for medical devices is preferably used to treat a surface of a medical device with the aid of heat and/or an acid.

The present invention also relates to a medical device, having an outer surface and/or an inner surface at least partially treated with the surface treatment agent for medical devices.

The present invention further relates to a catheter, having an outer surface and/or an inner surface at least partially treated with the surface treatment agent for medical devices.

Advantageous Effects of Invention

The surface treatment agents for medical devices of the present invention, which contain a copolymer of a hydrophilic functional group-containing monomer and an epoxy group-containing monomer, enable surfaces with a chemically fixed lubricant to be produced. Thus, treatment with such surface treatment agents enables medical devices such as catheters to have a surface with a lubricating polymer fixed thereon and, therefore, to get excellent lubricity and excellent lubricant durability after repeated movements, or in other words, durability that is so high that there will be little reduction in lubricity.

DESCRIPTION OF EMBODIMENTS

Figure 1:
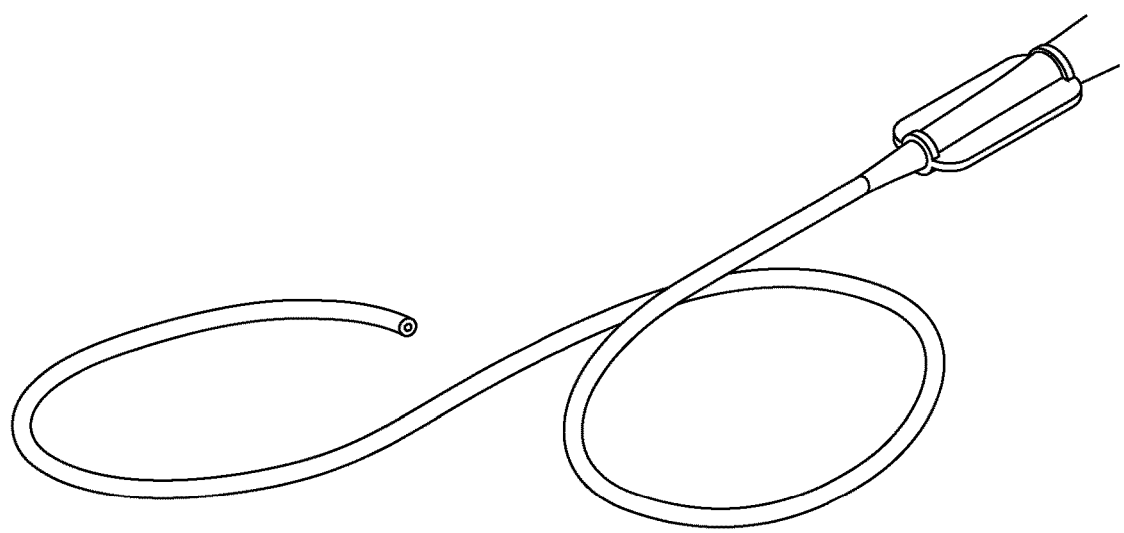
FIG. 1 is a schematic view of an example of a vascular catheter.
Figure 2:
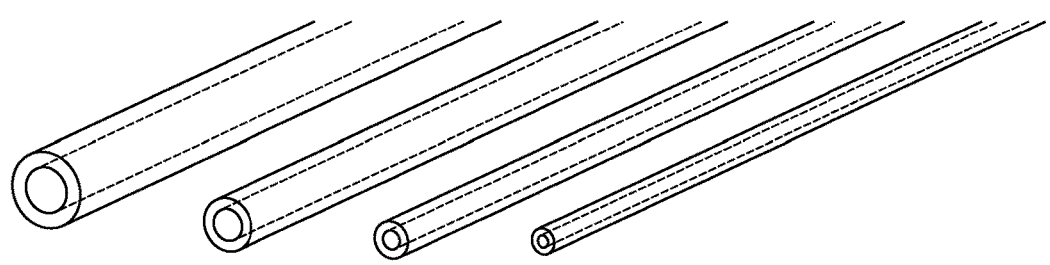
FIG. 2 is a schematic view showing examples of catheters with different diameters.

The surface treatment agents for medical devices of the present invention contain a copolymer of a hydrophilic functional group-containing monomer and an epoxy group-containing monomer. By chemically fixing such a copolymer to the surface of a medical device such as a catheter, it is possible to give it not only lubricity but also resistance to lubricity reduction (i.e., lubricant durability).

In the present invention, the constituent hydrophilic functional group-containing monomer of the copolymer is not particularly limited, and any monomers with various hydrophilic groups can be used. The hydrophilic functional group-containing monomer may suitably be a deliquescent monomer, i.e., a monomer having properties of spontaneously absorbing moisture (water vapor) from the air and forming an aqueous solution.

The hydrophilic functional group of the hydrophilic functional group-containing monomer is preferably a polyoxyalkylene group, a metal salt-containing hydrophilic group, a halogen salt-containing hydrophilic group, a zwitterionic group or the like in view of lubricity and its durability.

Suitable examples of the polyoxyalkylene group-containing monomer include compounds represented by the following formula (I):

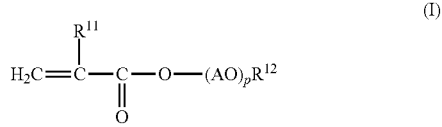

wherein AO groups are the same as or different from one another and each represent an oxyalkylene unit; $R^{11}$ represents a hydrogen atom or a methyl group; p represents an integer of 1 to 50; and $R^{12}$ represents a hydrogen atom or a C1 to C20 alkyl group.

The number of carbon atoms in each oxyalkylene unit (AO) is preferably 2 to 4 (e.g., oxyethylene unit, oxypropylene unit, oxytetramethylene unit). When different oxyalkylene units are present, they may be attached in blocks, randomly, or in an alternating fashion. Examples of C1 to C20 alkyl groups for $R^{12}$ include linear or branched groups such as methyl, ethyl, and propyl groups.

Specific examples of the polyoxyalkylene group-containing monomer include methoxypolyethylene glycol mono(meth)acrylate, polyethylene glycol mono(meth)acrylate, methoxypolypropylene glycol mono(meth)acrylate, polypropylene glycol mono(meth)acrylate, ethylene glycol-propylene glycol (meth)acrylate, and poly(ethylene glycol-propylene glycol) mono(meth)acrylate.

Suitable examples of the metal salt-containing hydrophilic group-containing monomer include monomers containing an alkali metal salt-containing hydrophilic group or an alkaline earth metal salt-containing hydrophilic group (alkali metal salt-containing monomers and alkaline earth metal salt-containing monomers).

Examples of alkali metal salt-containing monomers include alkali metal salts of acrylic acid such as sodium acrylate and potassium acrylate; alkali metal salts of methacrylic acid such as sodium methacrylate and potassium methacrylate; alkali metal salts of itaconic acid such as sodium itaconate and potassium itaconate; alkali metal salts of 3-vinylpropionic acid such as sodium 3-vinylpropionate and potassium 3-vinylpropionate; alkali metal salts of vinylsulfonic acid such as sodium vinylsulfonate and potassium vinylsulfonate; alkali metal salts of 2-sulfoethyl (meth)acrylate such as sodium 2-sulfoethyl (meth)acrylate and potassium 2-sulfoethyl (meth)acrylate; alkali metal salts of 3-sulfopropyl (meth)acrylate such as sodium 3-sulfopropyl (meth)acrylate and potassium 3-sulfopropyl (meth)acrylate; alkali metal salts of 2-acrylamide-2-methylpropanesulfonic acid such as sodium 2-acrylamide-2-methylpropanesulfonate and potassium 2-acrylamide-2-methylpropanesulfonate; and alkali metal salts of styrenesulfonic acid such as sodium styrenesulfonate and potassium styrenesulfonate.

Examples of alkaline earth metal salt-containing monomers include alkaline earth metal salt-containing monomers that correspond to the aforementioned alkali metal salt-containing monomers. In particular, alkali metal salts of (meth)acrylic acid are preferred, and potassium 3-sulfopropyl methacrylate is particularly preferred.

Suitable examples of the halogen salt-containing hydrophilic group-containing monomer include monomers containing a chlorine salt- or bromine salt-containing hydrophilic group (chlorine salt-containing monomers and bromine salt-containing monomers). In particular, preferred are compounds represented by the following formula (II) and the like:

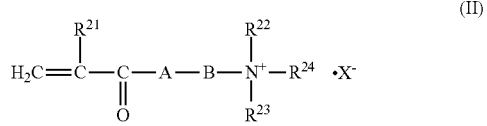

wherein A represents an oxygen atom or NH; B represents a C1 to C4 alkylene group; $R^{21}$ represents a hydrogen atom or a methyl group; $R^{22}$, $R^{23}$ and $R^{24}$ are the same as or different from one another and each represent a C1 to C4 alkyl group; and $X^-$ represents a halogen ion.

A is preferably an oxygen atom. Examples of B include linear or branched alkylene groups such as methylene, ethylene, and propylene groups. Methylene and ethylene groups are preferred among these. Examples of $R^{22}$ to $R^{24}$ include linear or branched alkyl groups such as methyl, ethyl, and propyl groups. Methyl and ethyl groups are preferred among these. Examples of X (halogen atom) include fluorine, chlorine, and bromine. Chlorine is preferred among these.

Examples of halogen salt-containing hydrophilic group-containing monomers represented by the formula (II) include 2-(methacryloyloxy)ethyl trimethylammonium chloride (2-(methacryloyloxy)ethyl trimethylaminium chloride), 2-(acryloyloxy)ethyl trimethylammonium chloride (2-(acryloyloxy)ethyl trimethylaminium chloride), 2-(methacryloyloxy)ethyl dimethylethylammonium chloride (2-(methacryloyloxy)ethyl dimethylethylaminium chloride), and 2-(acryloyloxy)ethyl dimethylethylammonium chloride (2-(acryloyloxy)ethyl dimethylethylaminium chloride).

Examples of the zwitterionic group-containing monomer (zwitterionic group-containing compound: compound bearing a center of permanent positive charge and a center of negative charge) include various zwitterionic monomers such as carboxybetaines, sulfobetaines, and phosphobetaines. Other examples include compounds represented by formula (III) below, and in particular compounds represented by formula (IV) below are suitable.

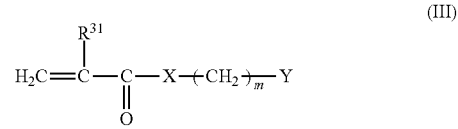

In the formula, $R^{31}$ represents —H or —CH$_3$; X represents —O—, NH— or N$^+$—; m represents an integer of 1 or greater; and Y represents a zwitterionic group or a halogen group (e.g. Cl$^-$, Br$^-$, F$^-$).

In the formula (III), $R^{31}$ is preferably —CH$_3$, X is preferably —O—, and m is preferably an integer of 1 to 10. In the zwitterionic group designated by Y, the cation may be a quaternary ammonium cation such as tetraalkylammonium, and the anion may be a carboxylate, sulfonate, phosphate or the like anion.

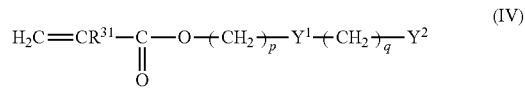

In the formula, $R^{31}$ represents —H or —CH$_3$; p and q each represent an integer of 1 or greater; and $Y^1$ and $Y^2$ are ionic functional groups with opposite charges.

In the formula (IV), p is preferably an integer of 2 or greater, and more preferably an integer of 2 to 10; and q is preferably an integer of 1 to 10, and more preferably an integer of 2 to 4. Moreover, preferred $R^{31}$ is the same as described above. $Y^1$ and $Y^2$ are as described for the cation and anion above.

Typical suitable examples of the zwitterionic monomer include compounds represented by the following formulae (IV-1) to (IV-4):

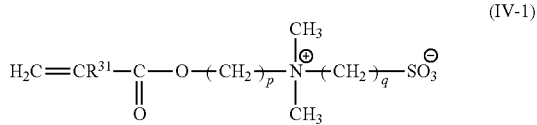

(IV-1)

wherein $R^{31}$ represents a hydrogen atom or a methyl group; and p and q each represent an integer of 1 to 10,

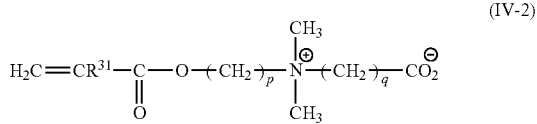

(IV-2)

wherein $R^{31}$ represents a hydrogen atom or a methyl group; and p and q each represent an integer of 1 to 10,

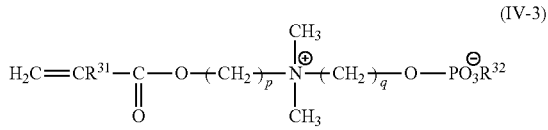

(IV-3)

wherein $R^{31}$ represents a hydrogen atom or a methyl group; $R^{32}$ represents a C1 to C6 hydrocarbon group; and p and q each represent an integer of 1 to 10,

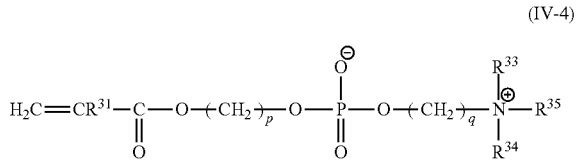

(IV-4)

wherein $R^{31}$ represents a hydrogen atom or a methyl group; $R^{33}$, $R^{34}$ and $R^{35}$ are the same as or different from one another and each represent a C1 or C2 hydrocarbon group; and p and q each represent an integer of 1 to 10.

Examples of compounds represented by the formula (IV-1) include dimethyl(3-sulfopropyl)(2-(meth)acryloyloxyethyl)-ammonium betaine. Examples of compounds represented by the formula (IV-2) include dimethyl(2-carboxyethyl)-(2-(meth)acryloyloxyethyl)ammonium betaine. Examples of compounds represented by the formula (IV-3) include dimethyl(3-methoxyphosphopropyl)(2-(meth)acryloyloxyethyl)-ammonium betaine. Examples of compounds represented by the formula (IV-4) include 2-(meth)acryloyloxyethyl phosphorylcholine. Other zwitterionic monomers include 2-(meth)acryloyloxyethyl carboxybetaine and 2-(meth)acryloyloxyethyl sulfobetaine.

The hydrophilic functional group-containing monomer may also be a quaternary ammonium salt monomer represented by the following formula:

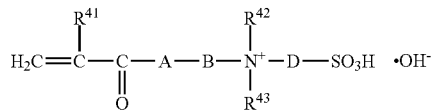

wherein A represents an oxygen atom or NH; B and D are the same as or different from each other and each represent a C1 to C4 alkylene group; $R^{41}$ represents a hydrogen atom or a methyl group; and $R^{42}$ and $R^{43}$ are the same as or different from each other and each represent a C1 to C4 alkyl group.

A is preferably an oxygen atom. Examples of B and D include linear or branched alkylene groups such as methylene, ethylene, and propylene groups. Methylene and ethylene groups are preferred among these. Examples of $R^{42}$ and $R^{43}$ include those described above for $R^{22}$ to $R^{24}$.

Examples of the quaternary ammonium salt monomer include [2-(methacryloyloxy)ethyl]dimethyl-(3-sulfopropyl)ammonium hydroxide. The hydrophilic functional group-containing monomers may be used alone or in combinations of two or more.

The constituent epoxy group-containing monomer of the copolymer in the present invention may be, for example, an epoxy group-containing polymerizable vinyl monomer containing an epoxy group and a polymerizable carbon-carbon double bond in the molecule.

Examples of the epoxy group-containing polymerizable vinyl monomer include epoxy group-containing (meth)acrylic acid ester monomers and epoxy group-containing ether monomers.

Examples of epoxy group-containing (meth)acrylic acid ester monomers include epoxy group-containing (meth)acrylic acid esters, specifically glycidyl (meth)acrylate, hydroxybutyl acrylate glycidyl ether and 2-methyloxiranylmethyl (meth)acrylate. Examples of epoxy group-containing ether monomers include epoxy group-containing linear, branched or cyclic aliphatic ether monomers such as vinyl glycidyl ether, allyl glycidyl ether, isopropenyl glycidyl ether, and 4-vinylcyclohexyl glycidyl ether; and epoxy group-containing aromatic ether monomers such as 3-vinylbenzyl glycidyl ether and 4-vinylbenzyl glycidyl ether. In view of lubricity and its durability, epoxy group-containing (meth)acrylic acid ester monomers are preferred among these, and glycidyl (meth)acrylate is particularly preferred. The epoxy group-containing monomers may be used alone or in combinations of two or more.

The copolymer of a hydrophilic functional group-containing monomer and an epoxy group-containing monomer can be produced by known radical polymerization processes. The copolymerization may be carried out by any process, such as, for example, known photo- or thermally-induced radical polymerization processes. Specifically, a photopolymerization initiator, a hydrophilic functional group-containing monomer and an epoxy group-containing monomer may be charged in liquid form or in the form of a solution into a transparent vessel made of glass, PET, polycarbonate or the like, followed by irradiation with UV light to allow radical polymerization (photo-radical polymerization) to proceed, whereby the copolymer can be prepared. The radical-polymerizable monomers (in liquid form) or solution thereof may contain a known polymerization inhibitor such as 4-methylphenol.

Examples of polymerization initiators include carbonyl compounds, organic sulfur compounds such as tetraethylthiuram disulfide, persulfides, peroxides, redox compounds, azo compounds, diazo compounds, halogen compounds, and photoreducing dyes. Among these, carbonyl compounds, peroxides, and azo compounds are preferred.

Preferred among carbonyl compounds serving as initiators for photo-induced radical polymerization are benzophenone and derivatives thereof (benzophenone compounds).

For example, suitable are benzophenone compounds represented by the following formula:

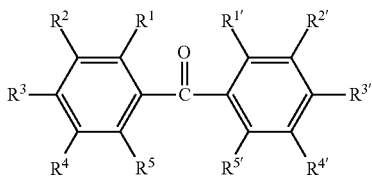

wherein $R^1$ to $R^5$ and $R^{1\prime}$ to $R^{5\prime}$ are the same as or different from one another and each represent a hydrogen atom, an alkyl group, a halogen (fluorine, chlorine, bromine, iodine), a hydroxyl group, a primary, secondary, or tertiary amino group, a mercapto group, or a hydrocarbon group that may contain an oxygen, nitrogen, or sulfur atom, and any two adjacent groups of $R^1$ to $R^5$ and $R^{1\prime}$ to $R^{5\prime}$ may be joined to each other to form a ring together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because these compounds allow polymer brushes to be formed well.

The initiator for photo-induced radical polymerization may also suitably be a thioxanthone compound because it provides a high polymerization rate and can easily be adsorbed on and/or reacted with rubber or the like. For example, suitable are compounds represented by the following formula:

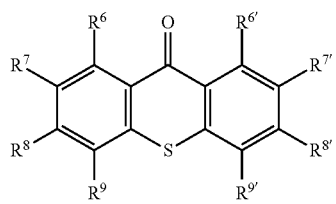

wherein $R^6$ to $R^9$ and $R^{6\prime}$ to $R^{9\prime}$ are the same as or different from one another and each represent a hydrogen atom, a halogen atom, or an alkyl, cyclic alkyl, aryl, alkenyl, alkoxy, or aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, and 2-p-octyloxyphenyl-4-ethylthioxanthone. Preferred among these are those which are substituted at one or two, especially two, of $R^6$ to $R^9$ and $R^{6\prime}$ to $R^{9\prime}$ with alkyl groups. More preferred is 2,4-diethylthioxanthone.

Light irradiation allows radical polymerization of the monomers to proceed. Here, ultraviolet light sources with an emission wavelength mainly in the ultraviolet region, such as high-pressure mercury lamps, metal halide lamps, and LED lamps, can be suitably used. The light dose may be appropriately chosen in view of polymerization time and uniform progress of the reaction. Moreover, in order to prevent inhibition of polymerization due to active gas such as oxygen in the reaction vessel and the reaction tube, oxygen is preferably removed from the reaction vessel, the reaction tube and the reaction solution during or before the light irradiation. To this end, appropriate operations may be performed. For example, an inert gas such as nitrogen gas or argon gas is inserted into the reaction vessel, the reaction tube and the reaction solution to discharge active gas such as oxygen from the reaction system and replace the atmosphere in the reaction system with the inert gas. Moreover, in order to prevent inhibition of the reaction due to oxygen or the like, for example, a measure may appropriately be taken in which an ultraviolet light source is placed such that no air layer (oxygen content: 15% or higher) exists between the reaction vessel made of glass, plastics or the like and the reaction solution or the modification target.

The ultraviolet wavelength suitably ranges from 300 to 400 nm. Such a wavelength allows a polymer to be formed well. Examples of light sources that can be used include high-pressure mercury lamps, LEDs with a center wavelength of 365 nm, and LEDs with a center wavelength of 375 nm. More preferred is irradiation with LED light having a wavelength of 355 to 380 nm. In particular, LEDs or the like having a center wavelength of 365 nm, which is close to the excitation wavelength (366 nm) of benzophenone, are preferred in view of efficiency. Light with a wavelength of 300 nm or longer is preferred, with light having a wavelength of 355 nm or longer being more preferred. Light having a wavelength of longer than 400 nm, however, is less likely to activate the photopolymerization initiator, with the result that the polymerization reaction is not allowed to easily proceed. Thus, light having a wavelength of 400 nm or shorter is preferred. Although LED light is suitable in that it is in a narrow wavelength range and does not include light with other wavelengths than the center wavelength, a mercury lamp or the like can also achieve similar effects to LED light by using a filter to block light having a wavelength of shorter than 300 nm.

Preferred among initiators for thermally-induced radical polymerization are peroxides and azo compounds.

"Peroxide" refers to those containing a —O—O— group, and examples include peroxyesters, peroxyketals, dialkyl peroxides, diacyl peroxides, and peroxycarbonates. In particular, organic peroxides such as benzoyl peroxide (BPO) and lauroyl peroxide (LPO) are preferred.

"Azo compound" refers to those containing a —N═N— group, and examples include 2,2'-azobis(4-methoxy-2,4-dimethylvaleronitrile), 2,2'-azobis(2,4-dimethylvaleronitrile), 2,2'-azobis(isobutyronitrile) (AIBN), 2,2'-azobis(2-methylbutyronitrile), 1,1'-azobis(cyclohexane-1-carbonitrile), 1-[(1-cyano-1-methylethyl)azo]formamide, 2,2'-azobis[2-(2-imidazolin-2-yl)propane]dihydrochloride, 2,2'-azobis[2-(2-imidazolin-2-yl)propane]disulfate dihydrate, 2,2'-azobis[2-(2-imidazolin-2-yl)propane], 2,2'-azobis(2-amidinopropane)dihydrochloride, and 2,2'-azobis[N-(2-carboxyethyl)-2-methylpropionamidine] n-hydrate. Among these, azobisisobutyronitrile (AIBN) and the like are preferred.

In addition to the copolymer prepared, for example, as described above, the surface treatment agents for medical devices of the present invention may contain additional components such as a solvent in amounts that do not impair the effects.

Examples of objects (medical devices) to be treated with the surface treatment agents for medical devices include thermoplastic elastomers such as nylon, polyester, and polyurethane, and dynamically crosslinked thermoplastic elastomers prepared from these elastomers. Examples of nylon include nylon 6, nylon 66, nylon 11, and nylon 12. Moreover, the dynamically crosslinked thermoplastic elastomer is preferably obtained by dynamically crosslinking a halogenated butyl rubber in a thermoplastic elastomer. In this case, the thermoplastic elastomer is preferably nylon, polyurethane, or the like.

Medical devices of the present invention can be prepared by treating the surface of a medical device with the surface treatment agent described above, and examples include those obtained by at least partially treating the outer surface and/or inner surface of a medical device with the surface treatment agent.

The treatment with the surface treatment agent may be carried out by any method that allows the surface treatment agent to make contact with the surface of a medical device, and examples include a method in which the treatment agent is fixed to the surface of a medical device by coating, spraying, immersion or the like. In particular, for fixing on the surface, the surface treatment is preferably carried out with the aid of heat and/or an acid. The treatment with heat may be carried out, for example, at 80° C. to 130° C. for 10 minutes to 10 hours. The treatment with an acid may be carried out using an inorganic or organic acid or the like appropriately chosen for fixing and the like.

The treatment is preferably applied to an area that requires lubricity, and the treatment may be applied to the entire surface. Particularly preferred examples of medical devices of the present invention are catheters, and the present invention gives them not only lubricity but also lubricant durability.

EXAMPLES

The present invention is more specifically described with reference to examples below. The present invention is, however, not limited to these examples.

Example 1

To a solution mixture of 5 ml of water and 4 ml of ethanol were added 0.65 g of an 80% aqueous solution of trimethyl-2-methacryloyloxyethyl ammonium chloride (an 80% aqueous solution of 2-(methacryloyloxy)ethyl trimethylammonium chloride) and 0.36 g of glycidyl methacrylate. To this was added 1 ml of a solution of benzophenone in methanol (2 mg/10 ml methanol), and the mixture was put in a 20-ml vial. The vial was covered with a lid and purged with a flow of Ar gas. Then, polymerization was carried out with stirring by irradiation from a 365 nm UV-LED (5 mW/cm$^2$) (irradiation time: 6 hours).

The surface of a tube made of nylon 12 was coated with the resulting polymer and held at 100° C. for 5 hours to fix the polymer. Thus, a surface-treated tube was prepared.

Example 2

To a solution mixture of 5 ml of water and 4 ml of ethanol were added 0.91 g of an 80% aqueous solution of trimethyl-2-methacryloyloxyethyl ammonium chloride and 0.21 g of glycidyl methacrylate. To this was added 1 ml of a solution of benzophenone in methanol (2 mg/10 ml methanol), and the mixture was put in a 20-ml vial. The vial was covered with a lid and purged with a flow of Ar gas. Then, polymerization was carried out with stirring by irradiation from a 365 nm UV-LED (5 mW/cm$^2$) (irradiation time: 3 hours).

The surface of a tube made of nylon 12 was coated with the resulting polymer and held at 100° C. for 5 hours to fix the polymer. Thus, a surface-treated tube was prepared.

Example 3

To a solution mixture of 5 ml of water and 4 ml of ethanol was added 0.91 g of an 80% aqueous solution of trimethyl-2-methacryloyloxyethyl ammonium chloride. To this was added 1 ml of a solution of benzophenone in methanol (2 mg/10 ml methanol), and the mixture was put in a 20-ml vial. The vial was covered with a lid and purged with a flow of Ar gas. Then, polymerization was carried out with stirring by irradiation from a 365 nm UV-LED (5 mW/cm$^2$) (irradiation time: 2.5 hours).

Thereafter, 0.21 g of glycidyl methacrylate dissolved in 1.5 ml of water and 1 ml of ethanol was added, and the resulting mixture was further subjected to irradiation from a UV-LED (5 mW/cm$^2$) for 1 hour.

The surface of a tube made of nylon 12 was coated with the resulting polymer and held at 100° C. for 5 hours to fix the polymer. Thus, a surface-treated tube was prepared.

Example 4

To a solution mixture of 5 ml of water and 4 ml of ethanol were added 0.62 g of potassium 3-(methacryloyloxy)propanesulfonate (potassium 3-sulfopropyl methacrylate) and 0.36 g of glycidyl methacrylate. To this was added 1 ml of a solution of benzophenone in methanol (2 mg/10 ml methanol), and the mixture was put in a 20-ml vial. The vial was covered with a lid and purged with a flow of Ar gas. Then, polymerization was carried out with stirring by irradiation from a 365 nm UV-LED (5 mW/cm$^2$) (irradiation time: 3 hours).

The surface of a tube made of nylon 12 was coated with the resulting polymer and held at 100° C. for 5 hours to fix the polymer. Thus, a surface-treated tube was prepared.

Example 5

To a solution mixture of 5 ml of water and 4 ml of ethanol were added 0.71 g of [2-(methacryloyloxy)ethyl]dimethyl-(3-sulfopropyl)ammonium hydroxide and 0.36 g of glycidyl methacrylate. To this was added 1 ml of a solution of benzophenone in methanol (2 mg/10 ml methanol), and the mixture was put in a 20-ml vial. The vial was covered with a lid and purged with a flow of Ar gas. Then, polymerization was carried out with stirring by irradiation from a 365 nm UV-LED (5 mW/cm$^2$) (irradiation time: 3 hours).

The surface of a tube made of nylon 12 was coated with the resulting polymer and held at 100° C. for 5 hours to fix the polymer. Thus, a surface-treated tube was prepared.

Example 6

An amount of 5.8 g of trimethyl-2-methacryloyloxyethyl ammonium chloride and 1.07 g of glycidyl methacrylate were dissolved in 25 ml of ethanol. To this was added 0.05 g of AIBN, and the mixture was put in a 20-ml vial. The vial was covered with a lid and purged with a flow of Ar gas. Then, the vial was placed in a water bath at 60° C., and polymerization was carried out for 4 hours with stirring.

The surface of a tube made of nylon 12 was coated with the resulting polymer and held at 100° C. for 5 hours to fix the polymer. Thus, a surface-treated tube was prepared.

Example 7

An amount of 5.8 g of trimethyl-2-methacryloyloxyethyl ammonium chloride and 1.07 g of glycidyl methacrylate were dissolved in 25 ml of ethanol. To this was added 0.07 g of benzoyl peroxide (BPO), and the mixture was put in a 20-ml vial. The vial was covered with a lid and purged with a flow of Ar gas. Then, the vial was placed in a water bath at 60° C., and polymerization was carried out for 4 hours with stirring.

The surface of a tube made of nylon 12 was coated with the resulting polymer and held at 100° C. for 5 hours to fix the polymer. Thus, a surface-treated tube was prepared.

Comparative Example 1

A tube made of nylon 12 was used as it was.

Comparative Example 2

Used was a tube made of nylon 12, the surface of which was coated with a 5% solution of methyl vinyl ether-maleic anhydride (GANTREZ-AN 16, produced by IPS) in methanol. It should be noted that nylon 12 is a material often used in vascular catheters, and methyl vinyl ether-maleic anhydride is a typical lubricant to provide the surface with lubricity.

The surface-treated tubes prepared in the examples and comparative examples were evaluated as follows.
(Lubricity)

Water was applied to the surface of each tube, and the sliding properties of the surface were then subjectively evaluated by touching with a human finger. The subjective evaluation was carried out by ten persons according to the following rating scale of 1-5: a rating of 5 corresponds to a tube with good sliding properties and a rating of 1 corresponds to a tube with so poor sliding properties that the finger never slides on the surface. The average rating was calculated.
(Lubricant Durability)

After water was applied to the surface of each tube, the tube was held between fingers and moved by sliding on the fingers. This cycle was repeated 100 times. Then, the subjective evaluation was again carried out by ten persons according to the rating scale for lubricity, and the average rating and the rate of decrease from the initial lubricity were calculated.

TABLE 1

| | Example 1 | Example 2 | Example 3 | Example 4 | Example 5 | Example 6 | Example 7 | Comparative Example 1 | Comparative Example 2 |
|---|---|---|---|---|---|---|---|---|---|
| Lubricity | 4.2 | 4.3 | 4.4 | 4.6 | 4.2 | 4.3 | 4.2 | 1 | 4.1 |
| Durability | 4.1 | 4.2 | 4.3 | 4.3 | 4.1 | 4.2 | 4.1 | 1 | 2.1 |
| Rate of decrease | 2.30% | 2.30% | 2.30% | 6.50% | 2.30% | 2.30% | 2.30% | 0% | 49% |

Table 1 shows that the nylon surfaces in the examples each had high lubricity, good durability, and quite a low rate of decrease in lubricity. In contrast, Comparative Example 1 had quite poor lubricity; Comparative Example 2, in which a commonly used product was used, had moderately high initial lubricity, but had low durability and quite a high rate of decrease in lubricity.

These results demonstrated that by using a surface treatment agent containing a copolymer of a hydrophilic functional group-containing monomer and an epoxy group-containing monomer and fixing the polymer on the surface of a catheter or the like, it is possible to simultaneously give it sufficient lubricity and lubricant durability.

The invention claimed is:

1. A medical device, having an outer surface and/or an inner surface at least partially treated with a surface treatment agent for medical devices, wherein
the surface treatment agent comprises a copolymer of a hydrophilic functional group-containing monomer and an epoxy group-containing monomer, and
the surface of the medical device is treated with the surface treatment agent and then exposed to heat at a temperature of 80° C. to 130° C. for 10 minutes to 10 hours.

2. The medical device according to claim 1, wherein the hydrophilic functional group is at least one selected from the group consisting of a polyoxyalkylene group, a metal salt-containing hydrophilic group, a halogen salt-containing hydrophilic group, and a zwitterionic group.

3. The medical device according to claim 2, wherein the metal salt-containing hydrophilic group is at least one selected from the group consisting of an alkali metal salt-containing hydrophilic group and an alkaline earth metal salt-containing hydrophilic group.

4. The medical device according to claim 2, wherein the halogen salt-containing hydrophilic group is a chlorine salt-containing hydrophilic group.

5. The medical device according to claim 1, wherein the copolymer is produced by photo- or thermally-induced radical polymerization.

6. The medical device according to claim 1, wherein the medical device is a catheter.

7. The medical device according to claim 2, wherein the epoxy group-containing monomer is selected from the group consisting of glycidyl (meth)acrylate, hydroxybutyl acrylate glycidyl ether, 2-methyloxiranylmethyl (meth)acrylate, vinyl glycidyl ether, allyl glycidyl ether, isopropenyl glycidyl ether, 4-vinylcyclohexyl glycidyl ether, 3-vinylbenzyl glycidyl ether and 4-vinylbenzyl glycidyl ether.

8. The medical device according to claim 7, wherein the hydrophilic functional group-containing monomer is a metal salt-containing hydrophilic group that comprises at least one selected from the group consisting of sodium acrylate, potassium acrylate, sodium methacrylate, potassium methacrylate, sodium itaconate, potassium itaconate, sodium 3-vinylpropionate, potassium 3-vinylpropionate, sodium vinylsulfonate, potassium vinylsulfonate, sodium 2-sulfoethyl (meth)acrylate, potassium 2-sulfoethyl (meth)acrylate, sodium 3-sulfopropyl (meth)acrylate, potassium 3-sulfopropyl (meth)acrylate, sodium 2-acrylamide-2-methylpropanesulfonate, potassium 2-acrylamide-2-methylpropanesulfonate, sodium styrenesulfonate, potassium styrenesulfonate, and potassium 3-sulfopropyl methacrylate.

9. The medical device according to claim 7, wherein the hydrophilic functional group-containing monomer is a quaternary ammonium salt monomer represented by the following formula:

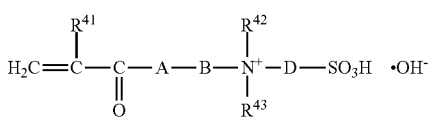

wherein A represents an oxygen atom or NH; B and D are the same as or different from each other and each represent a C1 to C4 alkylene group; $R^{41}$ represents a hydrogen atom or a methyl group; and $R^{42}$ and $R^{43}$ are the same as or different from each other and each represent a C1 to C4 alkyl group.

10. The medical device according to claim 7, wherein the hydrophilic functional group-containing monomer is a zwitterionic group containing monomer which comprises at least one member selected from the following formulae (IV-1) to (IV-4):

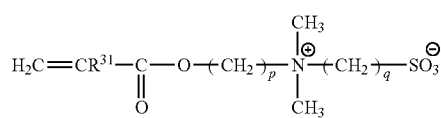
(IV-1)

wherein $R^{31}$ represents a hydrogen atom or a methyl group; and p and q each represent an integer of 1 to 10;

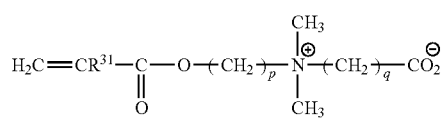
(IV-2)

wherein $R^{31}$ represents a hydrogen atom or a methyl group; and p and q each represent an integer of 1 to 10;

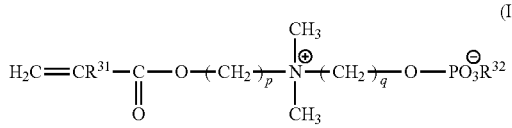
(IV-3)

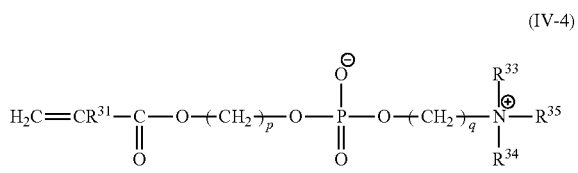

wherein $R^{31}$ represents a hydrogen atom or a methyl group; $R^{32}$ represents a C1 to C6 hydrocarbon group; and p and q each represent an integer of 1 to 10; and

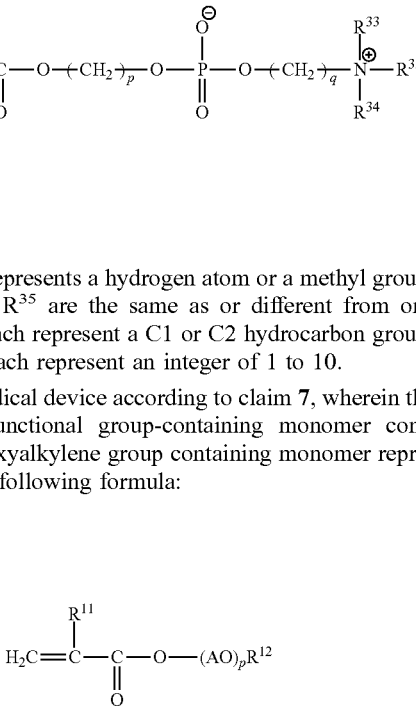
(IV-4)

wherein $R^{31}$ represents a hydrogen atom or a methyl group; $R^{33}$, $R^{34}$ and $R^{35}$ are the same as or different from one another and each represent a C1 or C2 hydrocarbon group; and p and q each represent an integer of 1 to 10.

11. The medical device according to claim 7, wherein the hydrophilic functional group-containing monomer comprises a polyoxyalkylene group containing monomer represented by the following formula:

(I)

wherein AO groups are the same as or different from one another and each represent an oxyalkylene unit; $R^{11}$ represents a hydrogen atom or a methyl group; p represents an integer of 1 to 50; and $R^{12}$ represents a hydrogen atom or a C1 to C20 alkyl group.

\* \* \* \* \*